US009027559B2

(12) United States Patent
Brain

(10) Patent No.: US 9,027,559 B2
(45) Date of Patent: *May 12, 2015

(54) LARYNGEAL MASK AIRWAY DEVICE WITH AIRWAY TUBE HAVING FLATTENED OUTER CIRCUMFERENCE AND ELLIPTICAL INNER AIRWAY PASSAGE

(75) Inventor: Archibald I. J. Brain, Victoria (SC)

(73) Assignee: The Laryngeal Mask Company Ltd., Victoria Mahe (SC)

( * ) Notice: Subject to any disclaimer, the term of this patent is extended or adjusted under 35 U.S.C. 154(b) by 0 days.

This patent is subject to a terminal disclaimer.

(21) Appl. No.: 13/268,730

(22) Filed: Oct. 7, 2011

(65) Prior Publication Data

US 2012/0024294 A1 Feb. 2, 2012

Related U.S. Application Data

(63) Continuation of application No. 11/904,188, filed on Sep. 26, 2007, now abandoned, which is a continuation of application No. 10/946,584, filed on Sep. 21, 2004, now abandoned, which is a continuation of application No. 10/348,813, filed on Jan. 22, 2003, now Pat. No. 6,792,948.

(51) Int. Cl.
*A61M 16/00* (2006.01)
*A61M 16/04* (2006.01)

(52) U.S. Cl.
CPC ........... *A61M 16/04* (2013.01); *A61M 16/0431* (2014.02); *A61M 16/0445* (2014.02)

(58) Field of Classification Search
CPC ............ A61M 16/04; A61M 16/0402; A61M 16/0431; A61M 16/0434; A61M 16/0461; A61M 16/0463; A61M 16/0465; A61M 16/0475; A61M 16/0477; A61M 16/0484; A61M 16/0486; A61M 16/06; A61M 16/10; A62B 7/00; A62B 7/02

USPC ............ 128/200.24, 204.18–204.23, 206.21, 128/206.29, 207.14–207.17

See application file for complete search history.

(56) References Cited

U.S. PATENT DOCUMENTS 2,862,498 A 12/1958 Weekes
3,554,673 A 1/1971 Schwartz et al.
(Continued)

FOREIGN PATENT DOCUMENTS

CA 2067782 6/1999
CA 2012750 8/1999
(Continued)

OTHER PUBLICATIONS

Abdelatti, "A Cuff Pressure Controller for Tracheal Tubes and Laryngeal Mask Airway," Anaesthesia, 1999, vol. 54, pp. 981-986.
(Continued)

*Primary Examiner* — Rachel Young
(74) *Attorney, Agent, or Firm* — Wilmer Cutler Pickering Hale and Dorr LLP

(57) ABSTRACT

The disclosed laryngeal mask airway device includes an inflatable cuff and an airway tube. The inflatable cuff defines a central opening at least when inflated. The cuff is insertable through a mouth of a patient to an inserted location within the patient. The cuff surrounds a glottic opening of the patient when the cuff is inflated and at the inserted location. The airway tube extends from a proximal end to a distal end. The airway tube defines an internal passage, an anterior portion, a posterior portion, a left portion, and a right portion. An airway passage extends from the proximal end of the tube through the internal passage to the glottic opening when the cuff is inflated and at the inserted location. The anterior portion is characterized by a thinner wall thickness than the left and right portions. The posterior portion is characterized by a thinner wall thickness than the left and right portions.

2 Claims, 6 Drawing Sheets

(56) References Cited

U.S. PATENT DOCUMENTS

| | | | |
|---|---|---|---|
| 3,683,908 A | 8/1972 | Michael et al. | |
| 3,931,822 A | 1/1976 | Marici | |
| 4,104,357 A | 8/1978 | Blair | |
| 4,222,378 A * | 9/1980 | Mahoney | 128/206.24 |
| 4,231,365 A | 11/1980 | Scarberry | |
| 4,256,099 A | 3/1981 | Dryden | |
| 4,453,545 A * | 6/1984 | Inoue | 128/207.15 |
| 4,509,514 A | 4/1985 | Brain | |
| 4,553,540 A | 11/1985 | Straith | |
| 4,793,327 A | 12/1988 | Frankel | |
| 4,821,715 A * | 4/1989 | Downing | 128/207.18 |
| 4,832,020 A | 5/1989 | Augustine | |
| 4,872,483 A | 10/1989 | Shah | |
| 4,953,547 A | 9/1990 | Poole, Jr. | |
| 4,995,388 A | 2/1991 | Brain et al. | |
| 5,038,766 A | 8/1991 | Parker | |
| 5,042,469 A | 8/1991 | Augustine | |
| 5,203,320 A | 4/1993 | Augustine | |
| 5,235,973 A | 8/1993 | Levinson | |
| 5,241,956 A | 9/1993 | Brain et al. | |
| 5,249,571 A | 10/1993 | Brain et al. | |
| 5,277,178 A | 1/1994 | Dingley et al. | |
| 5,282,464 A | 2/1994 | Brain et al. | |
| 5,297,547 A | 3/1994 | Brain et al. | |
| 5,303,697 A | 4/1994 | Brain et al. | |
| 5,305,743 A | 4/1994 | Brain | |
| 5,339,805 A | 8/1994 | Parker | |
| 5,339,808 A | 8/1994 | Don Michael | |
| 5,355,879 A | 10/1994 | Brain et al. | |
| 5,391,248 A | 2/1995 | Brain et al. | |
| 5,487,383 A | 1/1996 | Levinson | |
| 5,529,582 A | 6/1996 | Fukuhara et al. | |
| RE35,351 E | 10/1996 | Morgan et al. | |
| 5,569,219 A | 10/1996 | Hakki et al. | |
| 5,582,167 A | 12/1996 | Joseph | |
| 5,584,290 A | 12/1996 | Brain et al. | |
| 5,599,301 A | 2/1997 | Jacobs et al. | |
| 5,623,921 A | 4/1997 | Kinsinger et al. | |
| 5,632,271 A | 5/1997 | Brain et al. | |
| 5,653,229 A | 8/1997 | Greenberg | |
| 5,655,528 A | 8/1997 | Pagan et al. | |
| 5,682,880 A | 11/1997 | Brain et al. | |
| 5,694,929 A | 12/1997 | Christopher | |
| 5,711,293 A | 1/1998 | Brain et al. | |
| 5,738,094 A | 4/1998 | Hoftman | |
| 5,743,254 A | 4/1998 | Parker | |
| 5,743,258 A | 4/1998 | Sato et al. | |
| 5,746,202 A | 5/1998 | Pagan et al. | |
| 5,771,889 A | 6/1998 | Pagan et al. | |
| 5,791,341 A | 8/1998 | Bullard | |
| 5,832,920 A | 11/1998 | Field | |
| 5,850,832 A | 12/1998 | Chu | |
| 5,865,176 A | 2/1999 | O'Neil et al. | |
| 5,878,745 A | 3/1999 | Brain et al. | |
| 5,881,726 A | 3/1999 | Neame | |
| 5,896,858 A | 4/1999 | Brain | |
| 5,915,383 A | 6/1999 | Pagan | |
| 5,937,860 A | 8/1999 | Cook | |
| 5,979,445 A | 11/1999 | Neame et al. | |
| 5,983,897 A | 11/1999 | Pagan | |
| 5,988,167 A | 11/1999 | Kamen | |
| 5,996,582 A | 12/1999 | Turnbull | |
| 6,003,510 A | 12/1999 | Anunta | |
| 6,003,514 A | 12/1999 | Pagan | |
| 6,012,452 A | 1/2000 | Pagan | |
| 6,021,779 A | 2/2000 | Pagan | |
| 6,050,264 A | 4/2000 | Greenfield | |
| 6,070,581 A | 6/2000 | Augustine et al. | |
| 6,079,409 A | 6/2000 | Brain et al. | |
| D429,811 S | 8/2000 | Bermudez et al. | |
| 6,095,144 A | 8/2000 | Pagan | |
| 6,116,243 A | 9/2000 | Pagan | |
| 6,119,695 A | 9/2000 | Augustine et al. | |
| 6,152,136 A | 11/2000 | Pagan et al. | |
| 6,240,922 B1 | 6/2001 | Pagan | |
| 6,338,343 B1 | 1/2002 | Augustine et al. | |
| 6,390,093 B1 | 5/2002 | Mongeon | |
| 6,427,686 B2 | 8/2002 | Augustine et al. | |
| 6,439,232 B1 | 8/2002 | Brain | |
| 6,631,720 B1 | 10/2003 | Brain et al. | |
| 6,634,354 B2 | 10/2003 | Christopher | |
| 6,701,918 B2 | 3/2004 | Fariss et al. | |
| 6,705,318 B1 | 3/2004 | Brain | |
| 6,792,948 B2 | 9/2004 | Brain et al. | |
| 7,004,169 B2 | 2/2006 | Brain et al. | |
| 2001/0015207 A1 * | 8/2001 | Pagan | 128/207.15 |
| 2003/0051734 A1 | 3/2003 | Brain | |
| 2003/0131845 A1 | 7/2003 | Lin | |

FOREIGN PATENT DOCUMENTS

| | | |
|---|---|---|
| EP | 0 294 200 | 12/1988 |
| EP | 0 389 272 | 9/1990 |
| EP | 0 402 872 | 12/1990 |
| EP | 0 440 376 | 4/1992 |
| EP | 0 580 385 | 5/1996 |
| EP | 0712638 | 5/1996 |
| EP | 0732116 A2 | 9/1996 |
| EP | 0796631 | 9/1997 |
| EP | 0845276 | 6/1998 |
| EP | 0865798 | 9/1998 |
| EP | 0922465 | 6/1999 |
| EP | 1125595 | 8/2001 |
| EP | 1 119 386 B1 | 9/2005 |
| GB | 2111394 | 12/1982 |
| GB | 2205499 | 6/1987 |
| GB | 2298797 A | 9/1996 |
| GB | 2317342 | 3/1998 |
| GB | 2317830 | 4/1998 |
| GB | 2318735 | 5/1998 |
| GB | 2319478 | 5/1998 |
| GB | 2321854 | 8/1998 |
| GB | 2323289 | 9/1998 |
| GB | 2323290 | 9/1998 |
| GB | 2323291 | 9/1998 |
| GB | 2323292 | 9/1998 |
| GB | 2359996 | 9/2001 |
| JP | 10118182 | 5/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO-91/03207 | 3/1991 |
| WO | WO-91/07201 | 5/1991 |
| WO | WO-91/12845 | 9/1991 |
| WO | WO-92/13587 | 8/1992 |
| WO | WO-93/24170 | 12/1993 |
| WO | WO-95/33506 | 12/1995 |
| WO | WO-97/12640 | 4/1997 |
| WO | WO-97/12641 | 4/1997 |
| WO | WO-98/16273 | 4/1998 |
| WO | WO-99/06093 | 2/1999 |
| WO | WO-00/09189 | 2/2000 |
| WO | WO-00/22985 | 4/2000 |
| WO | WO-00/23135 | 4/2000 |
| WO | WO-00/61212 | 10/2000 |
| WO | WO-01/13979 | 3/2001 |

OTHER PUBLICATIONS

Benumof J.L., "Management of the difficult airway with special emphasis on awake tracheal intubation," *Anesthesiol*, 1991, 75;6:1087.

Benumof, "Laryngeal Mask Airway and the ASA Difficult Airway Algorithm," Anesthesiology, 1996, vol. 84(3), pp. 686-699.

Bernhard et al., "Adjustment of Intracuff Pressure to Prevent Aspiration," Anesthesiology, 1979, vol. 50(4), pp. 363-366.

(56) References Cited

OTHER PUBLICATIONS

Bernhard et al., "Physical Characteristics of and Rates of Nitrous Oxide Diffusion into Tracheal Tube Currs," Anesthesiology, 1978, vol. 48, pp. 413-414.
Brain, "The Laryngeal Mask—A New Concept in Airway Management," Br. J. Anaesth., 1983, vol. 55, pp. 801-805.
Brain, "The Laryngeal Mask Airway—A Possible New Solution to Airway Problems in the Emergency Situation," Archives of Emergency Medicine, 1984, vol. 1, pp. 229-232.
Brain, "The Laryngeal Mask Airway," Anaesthesia, 1985, vol. 40, pp. 356-361.
Brain, "Three Cases of Difficult Intuition Overcome by the Laryngeal Mask Airway," Anaesthesia, 1985, vol. 40, pp. 353-355.
Brain, et al., "A new laryngeal mask prototype," Anaesthesia, 1995, vol. 50, pp. 42-48.
Brimacombe, "The split laryngeal mask airway," Anaesthesia, 1993, vol. 48, p. 639.
Broderick et al., "The Laryngeal Mask Airway," Anaesthesia, 1989, vol. 44, pp. 238-241.
Burgard, et al., "The Effect of Laryngeal Mask Cuff Pressure on Postoperative Sore Throat Incidence," J. Clinical Anesthesia, 1996, vol. 8, pp. 198-201.
Caplan et al., "Adverse Respiratory Events in Anesthesia: A Closed Claims Analysis", Anesthesiology, 72:828-833, 1990.
Communication of a notice of opposition, European Patent Office, Feb. 15, 2006 (cover page and pp. 1-4).
Craven, "Prevention of Hospital-Acquried Pneumonia: Measuring Effect in Ounces, Pounds, and Tonds," Annals of Internal Medicine, 1995, vol. 122(3), pp. 229-231.
Craven, "Prevention of Hospital-Acquried Pneumonia: Measuring Effect in Ounces, Pounds, and Tons," Annals of Internal Medicine, 1995, vol. 122(3), pp. 229-231.
Cuff-Pressure-Control DCR, 2000, LogoMed (4 pages).
DeMello, et al., "The Use of the Laryngeal Mask Airway in Primary Anaesthesai," Anaesth. Corresp., 1990, vol. 45, pp. 629-633.
DeMello, et al., "The Use of the Laryngeal Mask Airway in Primary Anaesthesia," Anaesth. Corresp., 1990, vol. 45, pp. 793-794.
Doyle et al., "Intraoperative Awareness: A Continuing Clinical Problem," reprinted from Educational Synopses in Anesthesiology and Critical Care Medicine, The Online Journal of Anesthesiology vol. 3, No. 6, Jun. 1996, http://doyle.ibme.utoronoto.ca/anesthesia/aware.htm, 8 pages.
Engbers, "Practical Use of 'Diprifusor' Systems," Anaesthesia, 1998, vol. 53(1), pp. 28-34.
Eriksson et al., "Functional Assessment of the Pharynx at Rest and During Swallowing in Partially Paralyzed Humans," Anesthesiology, 1997, vol. 87(5), pp. 1035-1042.
Glen, "The Development of 'Diprifusor' : A TCI System for Propofol," Anaesthesia, 1998, vol. 53(1), pp. 13-21.
Gray et al., "Development of the Technology for 'Diprifusor' TCI Systems," Anaesthesia, 1998, vol. 53(1), pp. 22-27.
Heath, "Endotracheal Intubation Through the Laryngeal Mask—Helpful When Laryngoscopy is Difficult or Dangerous," European J. of Anaesthesiology, 1991, vol. 4, pp. 41-45.

Hickey, et al., "Cardiovascular Response to Insertion of Brain's Laryngeal Mask," Anaesthesia, 1990, vol. 45, pp. 629-633.
Inomata et al., "Transient Bilateral Vocal Cord Paralysis After Insertion of a Laryngeal Mask Airway," Anesthesiology, 1995, vol. 82, pp. 787-788.
Jacobson et al., "A Study of Intracuff Pressure Measurements, Trends and Behaviours in Patients During Prolonged Period of Tracheal Intubation," Br. J. Anaesth., 1981, vol. 53, pp. 97.
Kambic et al., "Intubation Lesions of the Larynx," Br. J. Anasth. 1978, vol. 50, pp. 587-590.
Kapila A., Addy E.V., Verghese C., Brain A.J., "Intubating LMA: a preliminary assessment of performance", *British Journal of Anesthesia*, 1995; 75:228-229 (abstract).
Lindholm, "Prolonged Endotracheal Intubation," ACTA Anaesthesiologica Scandinavica, 1969, vol. 33, pp. 32-46.
Majumder et al., "Bilateral Lingual Nerve Injury Following the Use of the Laryngeal Mask Airway," Anaesthesia, 1998, vol. 53, pp. 184-186.
Merriam Webster's Collegiate Dictionary 10th ed., 1997, pp. 591 and 975.
Merriam Webster's Collegiate Dictionary, 10th ed., 1997, pp. 254 & 1029, definirtions of Convex & Saddle.
Miller, "A pressure regulator for the cuff of a tracheal tube," Anaesthesia, 1992, vol. 47, pp. 594-596.
Muthuswamy et al., "The Use of Fuzzy Integrals and Bispectral Analysis of the Electroencephalogram to Predict Movement under Anesthesia," IEEE Transactions on Biomedical Engineering,1999, vol. 46(3), pp. 290-299.
Nagai, "Unilateral hypoglossal nerve paralysis following the use of the laryngeal mask airway," Anaesthesia, 1994, vol. 49, pp. 603-604.
Observations by Third Party Concerning European Patent Application No. 99 947 765.6-2318, European Patent Office, Munich, Germany, Jan. 18, 2005 (3 pgs.).
Patel et al., "Tracheal Tube Cuff Pressure," Anaesthesia, 1984, vol. 39, pp. 862-864.
Pennant, "Comparison of the Endotracheal Tube and Laryngeal Mask in Airway Managemet by Paramedical Personnel," Anesth. Analg. , 1992, vol. 74, pp. 531-534.
Pippin et al., "Long-Term Tracheal Intubation Practice in the United Kingdom," Anaesthesia, 1983, vol. 38, pp. 791-795.
Raeder et al. "Tracheal Tube Cuff Pressures," Anaesthesia, 1985, vol. 40, pp. 444-447.
Response to Complaint Matter No. 4b 0 440-05, In the Matter of: LMA Deutschland GmbH versus Ambu (Deutschland) GmbH, Feb. 10, 2006, pp. 1-47.
Seegobin et al., "Endotracheal Cuff Pressure and Tracheal Mucosal Blood Flow: Endoscopic Study of Effects of Four Large Volume Cuffs," British Medical Journal, 1984, vol. 288.
Willis et al., "Tracheal Tube Cuff Pressure," Anaesthesia, 1988, vol. 43, pp. 312-314.
Worthington, et al., "Proceedings of the Anaesthetic Research Society," Br. J. Anaesthesia, 1995, vol. 75, pp. 228P-229P.
Wynn et al., "Tongue Cyanosis After Laryngeal Mask Airway Insertion," Anesthesiology, 1994, vol. 80(6), pp. 1403.
Davies, et al., "Laryngeal mask airway and tracheal tube insertion by unskilled personnel," The Lancet, vol. 336, pp. 977-979. Oct. 1990.

* cited by examiner

LARYNGEAL MASK AIRWAY DEVICE WITH AIRWAY TUBE HAVING FLATTENED OUTER CIRCUMFERENCE AND ELLIPTICAL INNER AIRWAY PASSAGE

CROSS-REFERENCE SECTION

This application is a continuation of currently pending U.S. patent application Ser. No. 11/904188, filed Sep. 26, 2007, entitled Laryngeal Mask Airway Device with Airway Tube Having Flattened Outer Circumference and Elliptical Inner Airway Passage, which is a continuation of U.S. patent application Ser. No. 10/946,584, filed Sep. 21, 2004, and entitled Laryngeal Mask Airway Device With Airway Tube Having Flattened Outer Circumference and Elliptical Inner Airway Passage, which is a continuation of and claims priority to U.S. patent application Ser. No. 10/348,813, now U.S. Pat. No. 6,792,948, filed Jan. 22, 2003 and entitled Laryngeal Mask Airway Device With Airway Tube Having Flattened Outer Circumference and Elliptical Inner Airway Passage, the entire contents of which are incorporated herein by reference.

BACKGROUND OF THE INVENTION

The present invention relates to a laryngeal mask airway device. More specifically, the present invention relates to an improved airway tube for use with such devices.

The laryngeal mask airway device is a well known device that is useful for establishing airways in unconscious patients. Such devices have been in use for about thirteen years and offer an alternative to the older, even better known, endotracheal tube. For at least seventy years, endotracheal tubes comprising a long slender tube with an inflatable balloon disposed at the tube's distal end have been used for establishing airways in unconscious patients. In operation, the endotracheal tube's distal end is inserted through the mouth of the patient, past the patient's laryngeal inlet (or glottic opening), and into the patient's trachea. Once so positioned, the balloon is inflated so as to form a seal with the interior lining of the trachea. After this seal is established, positive pressure may be applied to the tube's proximal end to ventilate the patient's lungs. Also, the seal between the balloon and the inner lining of the trachea protects the lungs from aspiration (e.g., the seal prevents material regurgitated from the stomach from being aspirated into the patient's lungs).

Although they have been enormously successful, endotracheal tubes suffer from several major disadvantages. The principal disadvantage of the endotracheal tube relates to the difficulty of properly inserting the tube. Inserting an endotracheal tube into a patient is a procedure that requires a high degree of skill. Also, even for skilled practitioners, insertion of an endotracheal tube is sometimes difficult or not possible. In many instances, the difficulty of inserting endotracheal tubes has tragically led to the death of a patient because it was not possible to establish an airway in the patient with sufficient rapidity.

In addition to this principal disadvantage, there are also other disadvantages associated with endotracheal tubes. For example, intubation with an endotracheal tube often causes patients to suffer from severe "sore throats." The "sore throat" is principally caused by friction between the tube and the notch between the patient's arytenoid cartilages. Another disadvantage is that patients can not cough effectively while intubated with an endotracheal tube. Yet another problem with endotracheal tubes relates to the manner in which they are inserted. Inserting an endotracheal tube normally requires manipulations of the patient's head and neck and further requires the patient's jaw to be forcibly opened widely. These necessary manipulations make it difficult, or undesirable, to insert an endotracheal tube into a patient who may be suffering from a neck injury. Still another disadvantage is that endotracheal tubes provide an airway that is relatively small or narrow. The size of the airway must be relatively narrow because the distal end of the tube must be sufficiently small to fit into the trachea.

In contrast to the endotracheal tube, it is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulations of the patient's head, neck, and jaw. Further, the laryngeal mask airway device provides for ventilation of the patient's lungs without requiring contact with the sensitive inner lining of the trachea and the size of the airway established is typically significantly larger than the size of the airway established with an endotracheal tube. Also, the laryngeal mask airway device does not interfere with coughing to the same extent as endotracheal tubes. Largely due to these advantages, the laryngeal mask airway device has enjoyed increasing popularity over the last thirteen years.

FIGS. 1A and 1B show perspective and side views, respectively, of a prior art laryngeal mask airway device 100. FIG. 2 illustrates a device 100 that has been inserted into a patient. Laryngeal mask airway devices such as device 100 are described for example in U.S. Pat. No. 4,509,514. Laryngeal mask airway devices similar to device 100 have been marketed commercially as the "Classic" for many years by the Laryngeal Mask Company of Cyprus. Device 100 includes a flexible cylindrical airway tube 110 and a mask portion 130. Tube 110 extends from a proximal end 112 to a distal end 114 and mask portion 130 is coupled to the tube's distal end 114. Mask portion 130 includes a proximal end 132 and a generally elliptical inflatable cuff 134. Mask portion 130 also defines a central passageway extending from proximal end 132 to an open end 136 of cuff 134. The distal end 114 of tube 110 fits telescopically into the cylindrically shaped proximal end 132 of mask portion 130, and device 100 provides a continuous, sealed, airway extending from proximal end 112 of tube 110 to the open end 136 of cuff 134. Device 100 also includes an inflation tube 138 for selectively inflating or deflating cuff 134.

In operation, the cuff 134 is deflated, and then the mask portion is inserted through the patient's mouth into the patient's pharynx. The mask portion is preferably positioned so that a distal end 140 of cuff 134 rests against the patient's normally closed esophagus and so that the open end 136 of the cuff 134 is aligned with the entryway of the patient's trachea (i.e., the patient's glottic opening). After the mask portion is so positioned, the cuff is inflated thereby forming a seal around the patient's glottic opening and this establishes a sealed airway extending from the proximal end 112 of the tube 110 to the patient's trachea.

For convenience of exposition, the term "fully inserted configuration" shall be used herein to refer to a laryngeal mask airway device that has been inserted into a patient and has the following characteristics: (1) the mask portion is disposed around the patient's glottic opening; (2) the cuff is inflated forming a seal around the patient's glottic opening; and (3) the airway tube extends from a proximal end located outside the patient's mouth to a distal end that is coupled to the mask portion, the tube extending through the patient's mouth and the patient's natural upper airway so that the device provides a sealed airway extending from the tube's proximal end to the patient's lungs. FIG. 2 shows a laryngeal mask airway device in the fully inserted configuration.

When device 100 is in the fully inserted configuration, device 100 advantageously does not contact the interior lining of the trachea. Rather, the seal is established by contact between the tissues surrounding the patient's laryngeal inlet and the inflatable cuff 134. Unlike the delicate interior lining of the trachea, the tissues at the laryngeal inlet are accustomed to contact with foreign matter. For example, during the act of swallowing food, the food is normally squeezed against these tissues on its way to the esophagus. These tissues are accordingly less sensitive and less susceptible to being damaged by contact with the inflatable cuff.

U.S. Pat. No. 5,303,697 describes an example of another type of prior art device that may be referred to as an "intubating laryngeal mask airway device." The intubating device is useful for facilitating insertion of an endotracheal tube. After an intubating laryngeal mask airway device has been located in the fully inserted configuration, the device can act as a guide for a subsequently inserted endotracheal tube. Use of the laryngeal mask airway device in this fashion facilitates what is commonly known as "blind insertion" of the endotracheal tube. Only minor movements of the patient's head, neck, and jaw are required to insert the intubating laryngeal mask airway device. Once the device has been located in the fully inserted configuration, the endotracheal tube may be inserted with virtually no additional movements of the patient simply by inserting the endotracheal tube through the airway tube of the intubating laryngeal mask airway device. This stands in contrast to the relatively large motions of the patient's head, neck, and jaw that would be required if the endotracheal tube were inserted without the assistance of the intubating laryngeal mask airway device.

As shown in FIG. 2, when the device 100 is in the fully inserted configuration, the airway tube 110 assumes a curved profile that is principally defined by the shape of the patient's natural upper airway (i.e., the patient's natural airway passage defined by anatomical structures such as the hard and soft palettes and the pharynx that allows air to freely pass between the mouth and the glottic opening). For convenience of exposition, the term "inserted shape" will be used herein to refer to the shape assumed by the airway tube when a laryngeal mask airway device is in the fully inserted configuration and the terms "resting shape" or "resting configuration" will be used herein to refer to the shape assumed by the airway tube when no external forces are acting on the tube (e.g., when the device is not inserted into a patient and is simply at rest).

In intubating laryngeal masks, the airway tube is often formed from rigid or semi-rigid material and the tube's resting shape is often identical or nearly identical to the tube's inserted shape. However, it is not always desirable to form the airway tube out of rigid material. For example, use of rigid materials, such as metal, for the airway tube increases the cost of the device and may also complicate insertion of the device.

Other laryngeal mask airway devices, such as device 100, use a more flexible airway tube for which the resting shape is different, and substantially straighter, than the tube's inserted shape. Use of such flexible airway tubes can facilitate insertion, and reduce the cost, of the device. However, it also requires the airway tube to bend or flex during insertion and to remain in a flexed, or stressed, position for as long as the device remains in the patient. In device 100, the amount by which the airway tube flexes during insertion (or the difference between the tube's resting and inserted shapes) is reduced by manufacturing the tube such that its resting shape is slightly curved rather than straight. FIG. 1B shows the resting shape of the airway tube 110 of device 100.

Several factors influence the design of the airway tube for a flexible tube device such as device 100. The airway tube 110 should be sufficiently flexible to permit the tube to easily flex or bend between the resting and inserted shapes. However, the tube 110 should also be sufficiently stiff, or have sufficient strength, to resist formation of kinks when flexing to the internal shape. FIG. 3 shows an example of a tube that has formed a kink 180 as a result of bending the tube by an extreme amount. As is well known, the size of the internal passageway defined by any tube is dramatically decreased at any such kinks 180. The effects of kinks in tubes is commonly experienced in connection with garden hoses. For example, formation of a single kink in a garden hose can dramatically decrease the amount of water that can pass through the hose and be distributed by a sprinkler The effects of kinks are similar in laryngeal mask airway devices. Any kinks forming in the airway tube of a laryngeal mask airway device essentially close off the tube's airway passage and dramatically decrease the volume of air that can pass through the tube. Accordingly, it is very important to design the airway tube so that kinks in the tube do not form when the tube flexes to the internal shape. The tube should be flexible enough to permit relatively easy movement between the resting and internal shapes, but not so flexible as to cause formation of kinks when the tube is flexed to the internal shape.

Device 100 achieves this compromise with a generally cylindrical airway tube 110. If not for the pre-bend (shown in FIG. 1B) of the airway tube that makes the tube's central axis curved rather than straight when the tube is in its resting position, the tube would be essentially perfectly cylindrical. FIG. 4 shows a cross section of airway tube 110 taken along line 4-4 as shown in FIG. 1B. As shown in FIG. 4, the outer perimeter 110-$o$ of the airway tube 110 is circular. The inner perimeter 110-$i$ of tube 110, which defines the tube's internal airway passage, is also circular. Also, the inner and outer perimeters, 110-$i$ and 110-$o$, respectively, are centered about a common point C. The airway tube 110 may be fabricated from poly vinyl chloride (PVC) or silicone characterized by a durometer of about 50-80 Shore A. In adult male sizes, the inner radius (i.e., the distance from the center C to the inner perimeter 110-$i$) is substantially equal to 5 millimeters and the outer radius $R_o$, (i.e., the distance from the center C to the outer perimeter 110-$o$) is substantially equal to 7.5 millimeters, such that the thickness T of the wall of the airway tube 110 is substantially equal to 2.5 millimeters.

Although the airway tube 110 of device 100 achieves the desired compromise of being sufficiently flexible to permit easy insertion into a patient (and relatively easy flexing between the resting and internal shapes) and sufficiently stiff to prevent formation of kinks when bent to the inserted shape, the tube 110 is under stress whenever it is in the internal shape. This stress reflects the resilient airway tube's tendency to automatically return to its resting shape. As a result of this stress, a force F, as shown in FIG. 2, is applied to anatomical structures of the patient whenever the device 100 is in the fully inserted configuration.

There remains a need for improved airway tubes for use with laryngeal mask airway devices.

SUMMARY OF THE INVENTION

These and other objects are provided by laryngeal mask airway devices that are characterized by improved airway tube. The outer perimeter of the airway tube may define a flattened portion. The flattened portion may extend from near the distal end of the tube to near the proximal end of the tube. The inner perimeter of the airway tube may be characterized by an oval shape.

The tube geometry advantageously reduces forces applied by the device to the patient when the device is inserted within a patient. The tube geometry also advantageously increases the size of the airway passage provided by the tube. The tube geometry may also facilitate insertion of the device into a patient.

In one aspect, the invention provides a laryngeal mask airway device that includes an inflatable cuff and an airway tube. The inflatable cuff defines a central opening at least when inflated. The cuff is insertable through a mouth of a patient to an inserted location within the patient. The cuff surrounds a glottic opening of the patient when the cuff is inflated and at the inserted location. The airway tube extends from a proximal end to a distal end. The airway tube defines an internal passage, an anterior portion, a posterior portion, a left portion, and a right portion. An airway passage extends from the proximal end of the tube through the internal passage to the glottic opening when the cuff is inflated and at the inserted location. The anterior portion is characterized by a thinner wall thickness than the left and right portions. The posterior portion is characterized by a thinner wall thickness than the left and right portions.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE FIGURES

For a fuller understanding of the nature and objects of the present invention, reference should be made to the following detailed description taken in connection with the accompanying drawings in which the same reference numerals are used to indicate the same or similar parts wherein.

DETAILED DESCRIPTION OF EXEMPLARY EMBODIMENTS

Figure 6A:
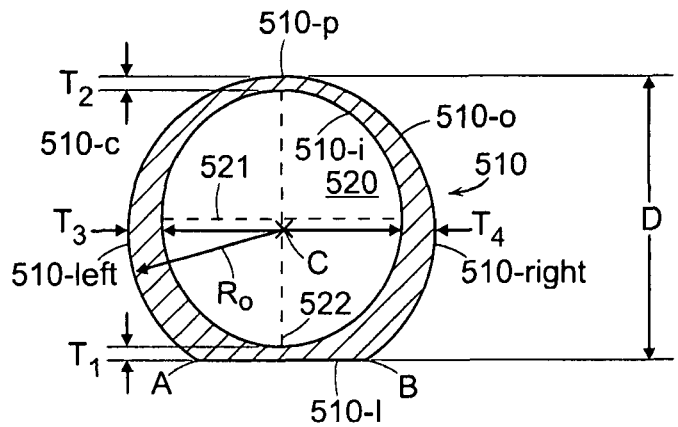
FIG. 6A shows a sectional view of the airway tube taken along the line 6A-6A as shown in FIG. 5B.
Figure 6B:
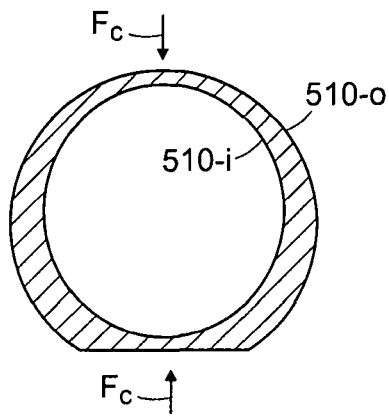
FIG. 6B shows a sectional view of the airway tube taken along the line 6B-6B as shown in FIG. 5C.
Figure 5A:
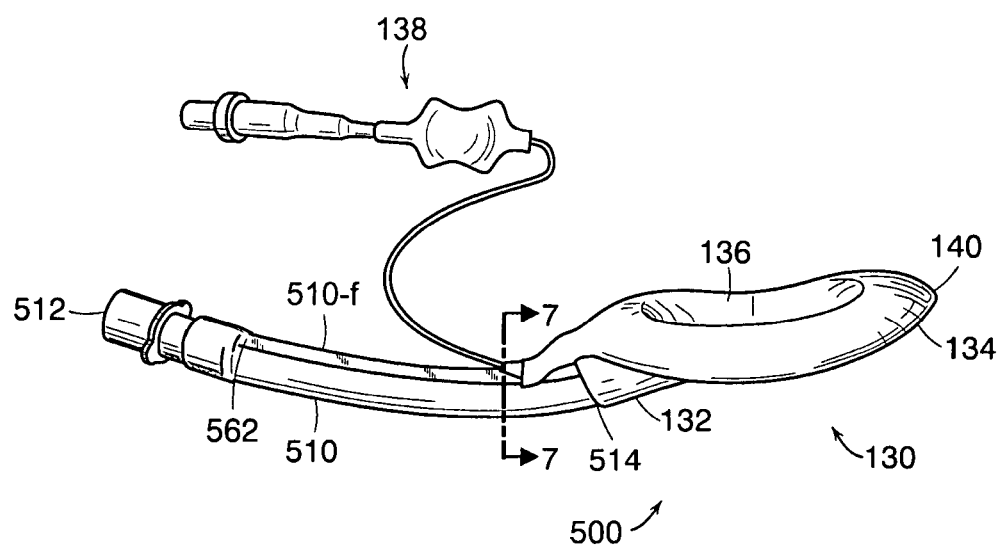
FIG. 5A shows a perspective view of a laryngeal mask airway device constructed according to the invention.
Figure 5B:
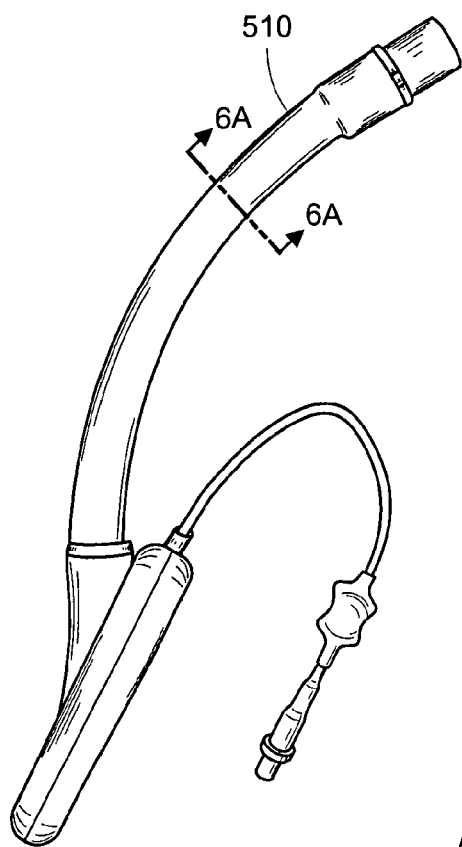
FIGS. 5B and 5C show side views of the device shown in FIG. 5A showing the resting shape and inserted shape, respectively, of the airway tube.
Figure 5C:
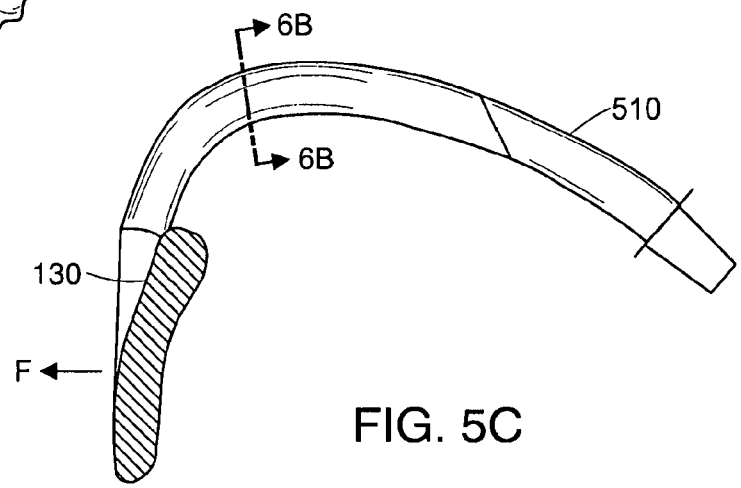

FIGS. 5A and 5B show perspective and side views, respectively, of a laryngeal mask airway device 500 constructed according to the invention when no external forces are acting on the device. FIG. 5C shows a side view of the shape assumed by device 500 when in the fully inserted configuration. So, FIGS. 5A and 5B show the resting shape of the device's airway tube and FIG. 5C shows the inserted shape of the device's airway tube. As shown, device 500 has many features in common with prior art device 100. However, instead of airway tube 110, device 500 includes an improved airway tube 510. FIG. 6A shows a sectional view of airway tube 510 taken along line 6A-6A as shown in FIG. 5B. FIG. 6B shows a sectional view of tube 510 taken along line 6B-6B as shown in FIG. 5C. So, FIGS. 6A and 6B show sectional views of resting and inserted shapes, respectively, of the airway tube 510.

As discussed in greater detail below, the airway tube 510 is distinct from prior art airway tube 110 in two principle respects. First, improved tube 510 defines a flattened portion 510-$f$ (shown, e.g., in FIG. 5A). Second, at least when tube 510 is in the resting shape, the inner perimeter of improved tube 510 is not circular; rather, it is oval, or characterized by the shape of an ellipse, as shown in FIG. 6A. As will be discussed further below, the construction of airway tube 510 advantageously reduces the force applied by the airway tube to sensitive anatomical structures of the patient when the device 500 is in the fully inserted configuration. The construction of airway tube 510 also advantageously reduces the tendency of the tube 510 to collapse, or form kinks, when flexed to the inserted shape and also maximizes the volume of the internal airway passage defined by the tube 510, thereby reducing flow resistance. Other advantages of device 500 will be discussed further below.

Figure 5D:
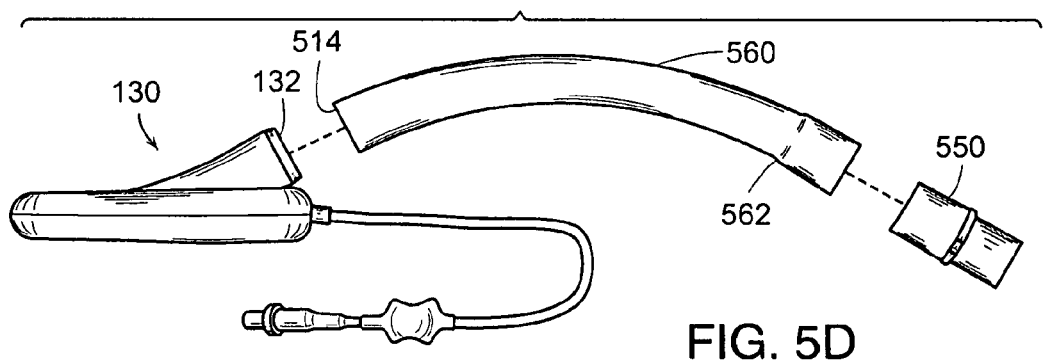
FIG. 5D shows the device shown in FIGS. 5A-C disassembled into some of its component parts.

FIG. 5D shows device 500 disassembled into some of its component parts. As shown, the airway tube 510 includes a connector section 550 and a tube section 560. Connector section 550 is preferably the same as that used in prior art devices. It is generally harder than tube section 560, its proximal end is designed to mate with standard ventilating devices, and its distal end fits telescopically into the proximal end of tube section 560. The proximal end of tube section 560 receives the distal end of connector section 550, and the distal end 514 of tube section 560 extends telescopically into a cylindrical opening defined by the proximal end 132 of mask portion 130. As shown in FIGS. 5A-D, the flattened portion 510-$f$ preferably extends from the distal end 514 of the tube section 560 to a location 562 of the tube section 560, location 562 being near the proximal end of the tube section 560.

As shown best in FIGS. 5A, 5B, and 6A, the outer perimeter 510-$o$ of airway tube 510 is not circular. Rather, the outer perimeter 510-$o$ is defined by two segments: a curved segment 510-$c$ and a linear segment 510-$l$. Curved segment 510-$c$ is a major arc of a circle defined by a center of curvature C and a radius $R_o$ and extends in a clockwise direction from point A to point B. Linear segment 510-$l$ is a substantially straight line defined by the shortest distance between points A and B. Presence of the linear segment 510-$l$ in the outer perimeter of airway tube 510 gives the tube a "flattened" appearance. As shown in FIGS. 5A-D, tube 510 defines a flattened portion 510-f that extends substantially from the distal end 514 to location 562.

Figure 1A:
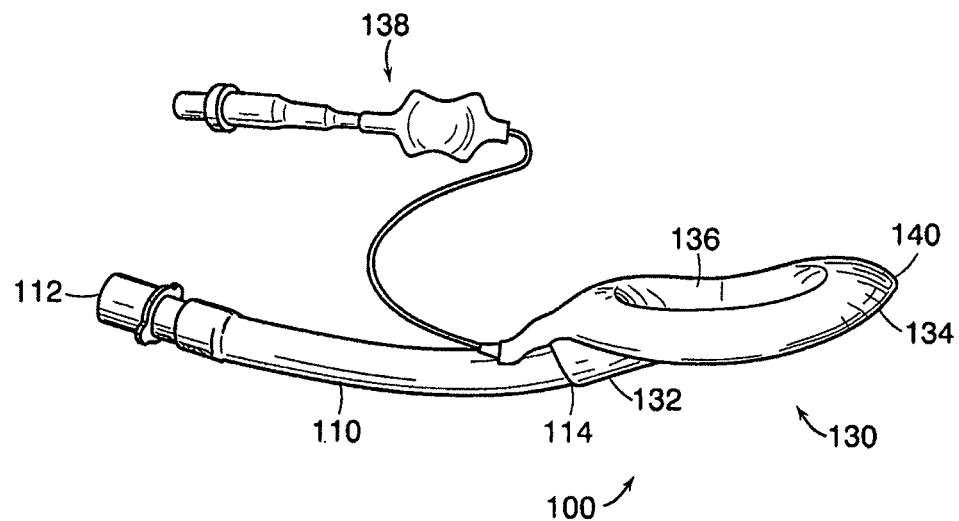
FIGS. 1A and 1B show perspective and side views, respectively, of a prior art laryngeal mask airway device.
Figure 1B:
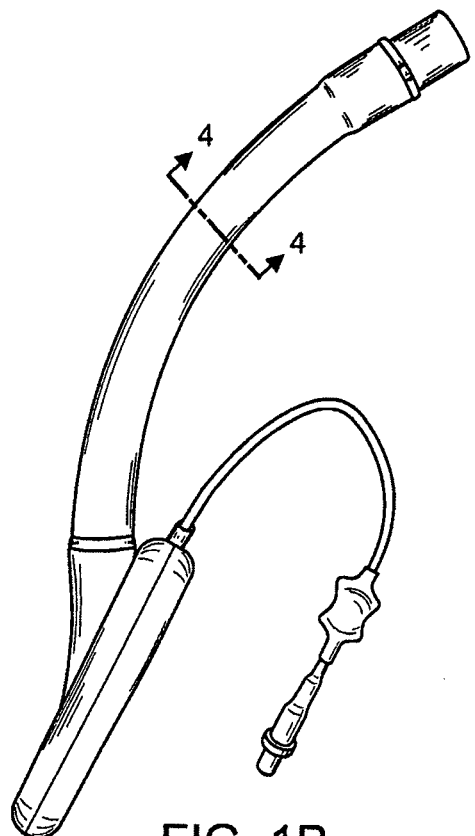
Figure 2:
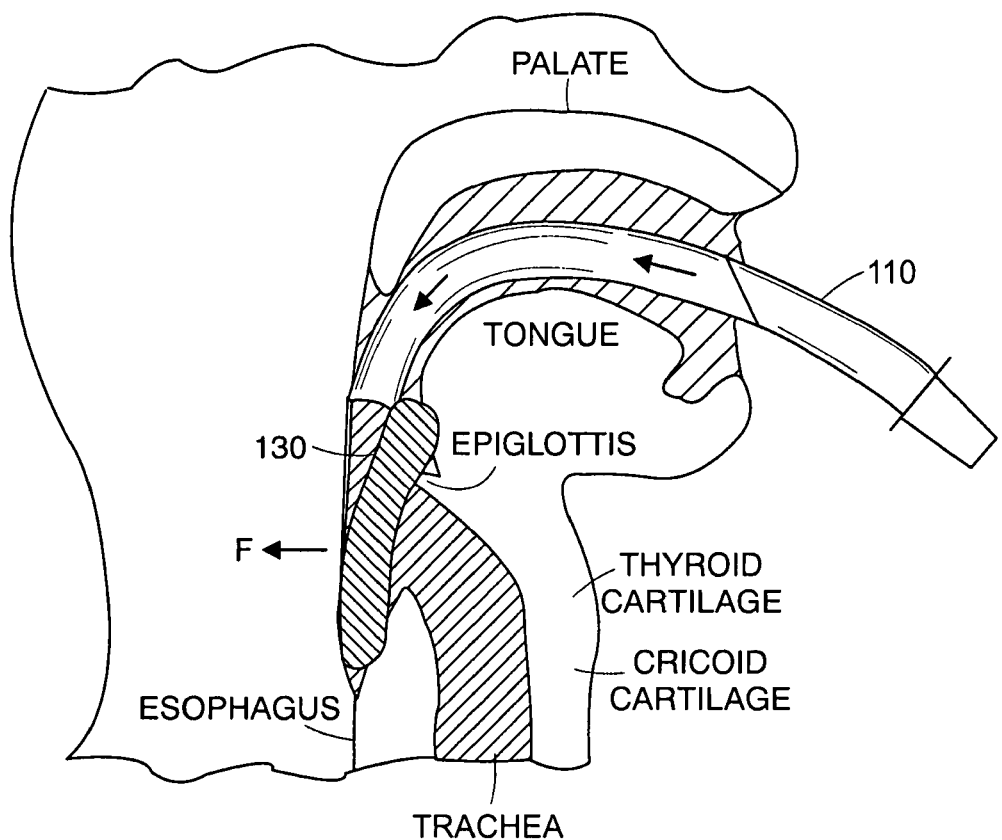
FIG. 2 shows the prior art device shown in FIGS. 1A and 1B in the fully inserted configuration.
Figure 3:
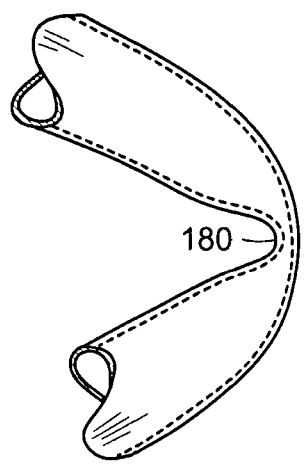
FIG. 3 shows a tube bent sufficiently to cause formation of a kink.

Airway tube 510 may be thought of as defining an anterior side, a posterior side, a left side, and a right side. Comparing FIGS. 6A, 5C, and 2, and in particular the part of FIG. 2 showing the portion of the airway tube near the mask portion, it may be seen that the flattened portion 510-f defines the anterior portion of the airway tube 510, and that the posterior portion 510-p is opposite to the flattened portion (i.e., since when device 500 is in the fully inserted configuration, the posterior portion 510-p will be adjacent to the patient's pharyngeal wall and the flattened portion 510-f near the mask portion 130 will be "forward" or anterior with respect to the posterior portion 510-p). The left and right portions of the airway tube, 510-left and 510-right, respectively, are also shown in FIG. 6A. It will be understood that the designations of anterior, posterior, left, and right are all made with respect to the device 500 when located in the fully inserted configuration.

Airway tube 510 defines an interior airway passage 520 that extends between the tube's proximal and distal ends. In tube section 560, the boundary of airway passage 520 is defined by an inner perimeter 510-i of the tube section 560. As noted above, at least when the tube 510 is in its resting shape, the inner perimeter 510-i of tube section 560 is oval. The oval inner perimeter 510-i is characterized by a short axis 521 and a long axis 522 (the short and long axes 521, 522 being shown in FIG. 6A by dashed lines). Short axis 521 extends between the left and right sides of the tube section 560. Long axis 522 extends between the anterior side 510-l and the posterior side 510-p of the tube section 560. As the names suggest, long axis 522 is longer than short axis 521, at least when tube 510 is in the resting position.

The oval inner perimeter 510-i is not centered on the center of curvature C of the curved segment 510-c. In FIG. 6A, the dashed horizontal line 521 bisects the airway passage 520 into equal sized upper and lower halves. As shown, this bisecting line 521 is offset from the center of curvature C and lies between the center of curvature C and the posterior portion 510-p.

As shown in FIG. 6A, the wall thickness of the anterior portion of the tube section 560 is $T_1$, the wall thickness of the posterior portion of the tube section 560 is $T_2$, the wall thickness of the left portion of the tube section 560 is $T_3$, and the wall thickness of the right portion of the tube section 560 is $T_4$. As a result of the tube's flattened posterior portion and the offset oval internal passage, the wall thicknesses of the anterior and posterior portions, $T_1$ and $T_2$, respectively, are thinner than the wall thicknesses of the left and right portions, $T_3$ and $T_4$, respectively. Preferably, the thickness of the anterior portion $T_1$ is substantially equal to the thickness of the posterior portion $T_2$. Also preferably, the thickness of the left portion $T_3$ is substantially equal to the thickness of the right portion $T_4$. In one preferred embodiment of an adult male size, the thicknesses $T_1$, $T_2$, $T_3$, and $T_4$ of the tube section 560 are substantially equal to 1.7 millimeters, 1.7 millimeters, 3.3 millimeters, and 3.3 millimeters, and the radius $R_o$ of curved segment 510-c is substantially equal to 7.5 millimeters. In that preferred embodiment, the tube section 560 of the airway tube 510 is made from PVC material characterized by a durometer in the range of 50-90 Shore A.

As illustrated generally in FIGS. 5A-C, and 2, when a resilient flexible airway tube is bent to the inserted shape, the tube naturally tends to spring back to its resting shape. This tendency causes a device in the fully inserted configuration to apply a force F to sensitive anatomical structures of the patient. Such a force does not present a significant concern when the duration of insertion is relatively short (e.g., a few minutes). However, in some circumstances it may be desirable to leave a laryngeal mask airway device in the fully inserted configuration for extended periods of several hours. Under these conditions, the force F applied to the patient (as shown in FIGS. 2 and 5C) is of concern and it is desirable to minimize it.

When a flexible airway tube is bent from its resting shape to its inserted shape, portions of the tube wall deform as a result. Specifically, at least part of the anterior portion of the tube is compressed and at least part of the posterior portion of the tube is elastically stretched, or placed under tension. The force F is principally generated in response to this compression and stretching in different parts of the airway tube. In general, the force generated by compressing or stretching an elastic member increases with the thickness of the member. When airway tube 510 is bent to the inserted shape, the maximum compression and stretching occur in the anterior portion 510-f and the posterior portion 510-p, respectively of tube section 560. The wall thicknesses of these portions of airway tube 510 (i.e., anterior portion 510-f and posterior portion 510-p) are by design reduced to a minimum. Reducing the wall thicknesses in areas of tube 510 that experience maximum compression and stretching advantageously reduces the force F generated by the tube and applied to the patient when the device is in the fully inserted configuration.

In addition to reducing trauma in the patient, reducing the force F also advantageously increases the stability of the laryngeal mask airway device 500. When a laryngeal mask airway device is in the fully inserted configuration, ideally there should be no forces acting on the device that may cause it to move relative to the patient. However, the force F can cause movement of the device within the patient. If the force F is large enough, or if it becomes combined with other forces resulting from patient movement or movement of the airway tube external to the patient, the resulting forces can cause the device to move within the patient. By reducing the force F to a minimum, device 500 advantageously reduces the likelihood that the device will move relative to the patient when in the fully inserted configuration.

As discussed above, reducing the wall thicknesses of the anterior portion 510-f and the posterior portion 510-p of the airway tube advantageously reduces the force F applied to the patient when the device 500 is in the fully inserted configuration. Also, reducing these wall thicknesses advantageously does not substantially affect the ability of tube 510 to resist forming kinks when the tube is bent to the inserted shape. This is because a tube's ability to resist forming kinks when the tube is bent is principally determined by the thickness of the left and right walls of the tube (because these left and right walls collapse in an outward direction when a kink is formed). In tube 510, the left and right walls of the airway tube are sufficiently thick to prevent kink formation and the anterior and posterior walls of the airway tube are sufficiently thin to reduce the force F applied to the patient.

Another advantageous feature of tube section 560 is that it is configured so as to provide support to the thinnest portions of tube section 560 (i.e., the anterior and posterior portions 510-f and 510-p) and thereby resist formation of kinks Referring to FIG. 6A, the portion of the tube above dashed line 521 is characterized by an "arched shape". The tube walls at the base of the arch (near dashed line 521) are thicker than the tube wall near the top of the arch (near posterior portion 510-p). This "arched shape" results from the oval, or elliptical, shape of the inner perimeter 510-i, and in particular from the long axis 522 of the ellipse being oriented so as to extend from the anterior portion to the posterior portion of the tube. The "arched shape" conveniently supports the relatively thin posterior portion 510-*p* and resists formation of kinks. Similarly, the portion of the tube below dashed line 521 is also characterized by an "arched shape" that supports the thin anterior portion and resists formation of kinks.

FIG. 6B illustrates yet another advantage of airway tube 510. Bending tube 510 into the inserted shape generates compressive forces $F_c$ that push on the anterior and posterior portions of the tube. As discussed above, tube 510 is configured so as to resist these compressive forces and prevent collapse of the tube, or formation of kinks in the tube. However, the compressive forces $F_c$ nonetheless have an effect on the geometry of tube 510. In particular, these compressive forces squeeze the tube and tend to make the inner perimeter 510-*i* more circular. That is, inner perimeter 510-*i* is oval when the tube 510 is in the resting shape. However, as tube 510 is forced into the inserted shape, the naturally oval inner perimeter 510-*i* is deformed into a more circular profile.

When the tube 510 is in the resting shape, inner perimeter 510-*i* is characterized by an oval shape and the long axis 522 (shown in FIG. 6A) of the inner perimeter extends between the anterior and posterior portions of the tube. The long axis 522 of the inner perimeter is aligned with the compressive forces that are generated by bending the tube to the inserted shape (or alternatively, the long axis 522 and the central axis of airway tube 510 both lie in a common plane regardless of whether the tube 510 is in the resting or inserted shape). Aligning the long axis 522 with these compressive forces advantageously shortens the inner perimeter in a direction aligned with the long axis when the tube is bent to the inserted shape and thereby causes the inner perimeter to deform to a more circular profile when the tube is bent to the inserted shape. The outer perimeter 510-*o*, which is generally circular (except for the flattened portion 510-*l*) when tube 510 is in the resting shape, is similarly deformed into a more oval profile. When prior art cylindrical tubes are bent into the inserted shape, both the inner and outer perimeters, which are circular in the resting shape, are deformed into oval profiles. So, when prior art airway tubes are forced into the inserted shape, their internal airway passages become narrowed, or oval, thereby making it harder to pass subsequently inserted catheters or endotracheal tubes and increasing resistance to flow of gas through them. However, when tube 510 is bent into the inserted shape, its internal airway passage deforms to a more circular shape thereby facilitating insertion of catheters or endotracheal tubes and preserving good flow characteristics.

Figure 4:
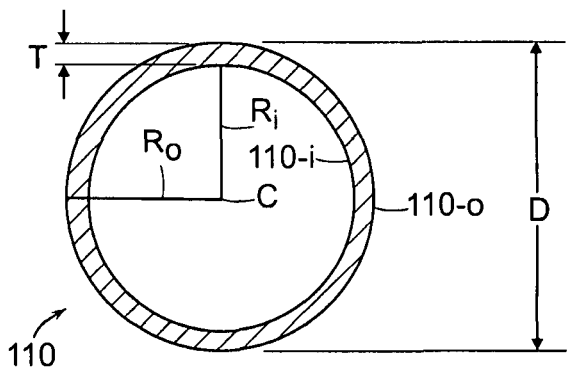
FIG. 4 shows a sectional view of the airway tube of the device shown in FIGS. 1A and 1B taken along line 4-4 as shown in FIG. 1B.

In addition to the above-described advantages, the configuration of airway tube 510 also advantageously provides an airway passage of increased cross sectional area in comparison to similarly sized prior art tubes. Referring to FIGS. 4 and 6A, the illustrated dimension D is the distance between the outer posterior and outer anterior portions of the airway tube. In the case of prior art tube 110 shown in FIG. 4, the distance D is simply the outer diameter of the tube. In the case of tube 510 shown in FIG. 6A, the distance D is not a "diameter", since the outer profile of the tube is not circular. However, in both tube 110 and tube 510, the distance D determines the inter-dental gap required to insert the tube (i.e., the space between the upper and lower teeth required to accommodate the airway tube, or the amount by which the patient must open their jaw to accommodate the tube). For any given distance D, the cross sectional area of airway passage 520 is greater than the cross sectional area of the airway passage provided by prior art tube 110. That is, a prior art cylindrical tube characterized by an outer diameter D provides an airway passage of reduced size as compared with the airway passage provided by a tube 510 characterized by the same dimension D. This is so because the wall thickness required in a prior art cylindrical tube to prevent kink formation results in an airway passage of decreased cross sectional area as compared with passage 520.

In general, it is desirable to minimize an airway tube's outer dimension D (and the corresponding inter-dental gap) while at the same time maximizing the area of the tube's airway passage. A large airway passage facilitates ventilation of the patient's lungs and also facilitates using the laryngeal mask airway device as an intubating device for guiding a subsequently inserted endotracheal tube.

As compared with prior art cylindrical tubes, airway tube 510 provides an airway passage 520 of enlarged area for any given outer dimension D. Accordingly, airway tube 510 may be configured to provide an internal airway passage having an area equal to that of a prior art tube while at the same time having a reduced outer dimension D. Laryngeal mask airway devices constructed using such airway tubes provide equivalent ventilation capacity while at the same time being easier to insert than a corresponding prior art device. Alternatively, airway tube 510 may be configured to provide an outer dimension D equal to that of a prior art cylindrical airway tube while at the same time providing an airway passage of enlarged area. Laryngeal mask airway devices constructed using such airway tubes are no more difficult to insert than corresponding prior art devices and yet advantageously provide increased ventilation capacity and permit intubation with a larger diameter endotracheal tubes.

Another advantage of airway tube 510 is that its flattened portion 510-*f* facilitates insertion of the device 500. Physicians normally insert laryngeal mask airway devices by placing an index finger on the device, near the junction of the airway tube and the mask portion, and by using the finger to apply pressure to the device and thereby push the mask portion through the patient's mouth and throat. Prior art cylindrical airway tubes make this type of insertion somewhat difficult because the physician's finger can easily slip off of the airway tube during insertion. The flattened portion 510-*f* of the airway tube 510 provides a stable platform for a physician's finger to rest on, and to apply pressure to, during insertion of the device.

Another advantage of device 500 relates to the use of insertion tools to control insertion of the device into a patient. A well known alternative to the use of a finger to control insertion is to use an "insertion tool". Such insertion tools generally have a distal end that attaches to the laryngeal mask airway device near a junction of the airway tube and the mask portion. Such insertion tools also generally have a proximal end that is gripped by the physician during insertion and that remains outside the patient's mouth during the entire insertion procedure.

Figure 7:
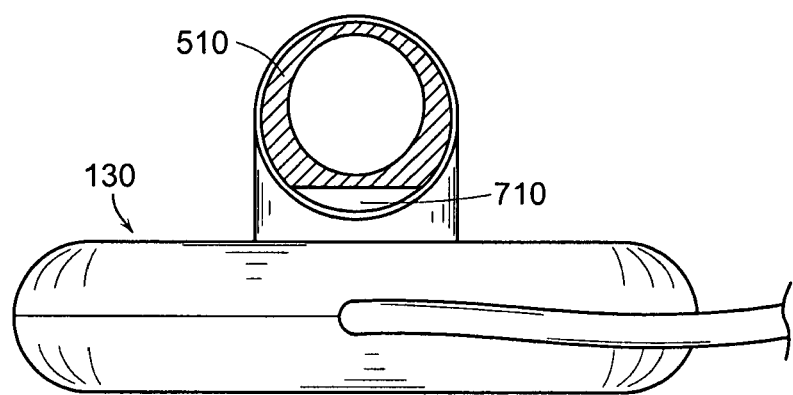
FIG. 7 shows a view of the intersection of the airway tube and mask portion of the device shown in FIG. 5A taken in the direction of line 7-7 as shown in FIG. 5A.

FIG. 7 shows a view of device 500 taken along line 7-7 as shown in FIG. 5A, and in particular shows a view of the device near the intersection of airway tube 510 and mask portion 130. As shown, the distal end of airway tube 510 fits telescopically into the cylindrical proximal end of mask portion 130. As shown, a gap 710 is defined between the flattened portion 510-*f* of tube 510 and the proximal end of mask portion 130. The gap 710 provides a convenient place for locating the distal end of an insertion tool during insertion of the device 500.

As noted above, FIG. 6A shows a sectional view of the tube section 560 when the tube is in the resting shape. The outer perimeter 510-*o* has been described as being bounded by a curved segment 510-*c* and a linear segment 510-*l*. In the preferred embodiment, the curved segment 510-*c* is a major arc of a circle centered about point C, and the linear segment 510-o is a chord of the circle that extends between the two endpoints of the major arc 510-c. However, it will be appreciated that airway tubes constructed according to the invention need not have this exact cross section and that the invention embraces generally airway tubes that define a flattened portion 510-f. For example, instead of being the major arc of a circle, the curved segment 510-c could follow an elliptical, or other non-circular, curve. Further, the curved segment 510-c need not be centered about a point C. Similarly, the linear segment 510-l need not be a straight line. Rather, it could also follow a curved, or arced, path. However, a radius of curvature of the linear segment 510-l is preferably significantly greater than that of the curved segment 510-c, or in other words, the linear segment 510-l is preferably straighter than curved segment 510-c. Also, cross sections taken at any point along a substantial length of the airway tube are preferably characterized by the union of a curved segment 510-c and a linear segment 510-l. Presence of a linear segment 510-l in cross sections taken at any point along a length of the tube in effect provide the tube with the desired flattened portion 510-f.

Similarly, while the preferred inner perimeter 510-i is oval, it will be appreciated that airway tubes construed according to the invention may be characterized by inner perimeters that have other types of curves. Preferably, the inner perimeter of the tube, when in the resting shape, is not circular and preferably a distance between the left and right sides of the inner perimeter is less than a distance between the anterior and posterior sides of the inner perimeter.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A laryngeal mask airway device, comprising:
(A) an inflatable cuff, the cuff defining a central opening at least when inflated, the cuff being insertable through a mouth of a patient to an inserted location within the patient, the cuff adapted to surround a glottic opening of the patient when inflated and at the inserted location;
(B) an airway tube extending from a proximal end to a distal end, the airway tube defining an offset oval internal airway passage, an anterior portion, a posterior portion, a left portion, and a right portion, the anterior portion being characterized by a thinner wall thickness than the left and right portions, the posterior portion being characterized by a thinner wall thickness than the left and right portions, a cross section of the airway tube having an outer perimeter, the outer perimeter including a curved segment and a linear segment, the curved segment extending from a first point to a second point, a portion of the airway tube being characterised by an arched shape wherein the tube walls at the base of the arch are thicker than the tube walls at the top of the arch opposite the linear segment, the linear segment extending from the first point to the second point, the outer perimeter of the airway tube having a flattened portion.

2. A laryngeal mask airway device, comprising:
(A) an inflatable cuff, the cuff defining a central opening at least when inflated, the cuff being insertable through a mouth of a patient to an inserted location within the patient, the cuff adapted to surround a glottic opening of the patient when inflated and at the inserted location;
(B) an airway tube extending from a proximal end to a distal end, the airway tube having an inner perimeter defining an internal airway passage, an anterior portion, a posterior portion, a left portion, and a right portion, the anterior portion being characterised by a thinner wall thickness than the left and right portions, the posterior portion being characterised by a thinner wall thickness than the left and right portions, a cross section of the airway tube having an outer perimeter, the outer perimeter including a curved segment and a linear segment, the curved segment extending from a first point to a second point, the linear segment extending from a first point to a second point, a portion of the airway tube being characterised by an arched shape wherein the tube walls at the base of the arch are thicker than the tube walls at the top of the arch opposite the linear segment, the outer perimeter of the airway tube having a flattened portion, wherein the internal airway passage is defined by an offset oval when the tube is in the resting shape and deformed into a more circular profile when the tube is forced into the inserted shape.

* * * * *